US010011831B2

(12) United States Patent
Pasloske et al.

(10) Patent No.: US 10,011,831 B2
(45) Date of Patent: *Jul. 3, 2018

(54) CRUDE BIOLOGICAL DERIVATIVES COMPETENT FOR NUCLEIC ACID DETECTION

(71) Applicant: APPLIED BIOSYSTEMS, LLC, Carlsbad, CA (US)

(72) Inventors: Brittan Pasloske, Austin, TX (US); Quoc Hoang, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/466,824

(22) Filed: Mar. 22, 2017

(65) Prior Publication Data

US 2017/0218359 A1  Aug. 3, 2017

Related U.S. Application Data

(63) Continuation of application No. 13/463,624, filed on May 3, 2012, now Pat. No. 9,611,497, which is a continuation of application No. 10/352,806, filed on Jan. 28, 2003, now abandoned.

(60) Provisional application No. 60/352,402.

(51) Int. Cl.
C12N 15/10 (2006.01)
C12Q 1/68 (2018.01)
C12P 19/34 (2006.01)
C12Q 1/6806 (2018.01)

(52) U.S. Cl.
CPC ..... *C12N 15/1096* (2013.01); *C12N 15/1003* (2013.01); *C12P 19/34* (2013.01); *C12Q 1/6806* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,596,789 A | 6/1986 | Dutta et al. |
| 4,691,007 A | 9/1987 | Dutta et al. |
| 4,910,190 A | 3/1990 | Bergeson et al. |
| 4,997,932 A | 3/1991 | Reardon et al. |
| 5,008,245 A | 4/1991 | Digenis |
| 5,194,588 A | 3/1993 | Edwards et al. |
| 5,284,829 A | 2/1994 | McKerrow et al. |
| 5,364,763 A | 11/1994 | Kacian |
| 5,386,024 A | 1/1995 | Kacian et al. |
| 5,414,132 A | 5/1995 | Stein et al. |
| 5,554,516 A | 9/1996 | Kacian et al. |
| 5,693,467 A | 12/1997 | Roblin, III et al. |
| 5,726,021 A | 3/1998 | Britschgi et al. |
| 5,726,158 A | 3/1998 | Edwards et al. |
| 5,871,628 A | 2/1999 | Dabiri et al. |
| 5,871,975 A | 2/1999 | Kacian et al. |
| 5,891,636 A | 4/1999 | Van Gelder et al. |
| 5,907,068 A | 5/1999 | Stein et al. |
| 5,939,262 A | 8/1999 | Pasloske et al. |
| 6,111,096 A | 8/2000 | Laugharn et al. |
| 6,204,375 B1 | 3/2001 | Lader |
| 6,218,105 B1 | 4/2001 | Hall et al. |
| 6,218,523 B1 | 4/2001 | French et al. |
| 6,218,531 B1 | 4/2001 | Ekenberg |
| 6,265,165 B1 | 7/2001 | Xu et al. |
| 6,313,285 B1 | 11/2001 | Butler et al. |
| 6,329,179 B1 | 12/2001 | Kopreski |
| 6,528,641 B2 | 3/2003 | Lader |
| 6,583,301 B1 | 6/2003 | Eaton et al. |
| 6,610,475 B1 | 8/2003 | Kacian et al. |
| 6,664,379 B1 | 12/2003 | Kudlicki et al. |
| 6,740,647 B1 | 5/2004 | Baucke et al. |
| 6,825,340 B2 | 11/2004 | Pasloske et al. |
| 7,001,724 B1 | 2/2006 | Greenfield |
| 7,067,298 B2 | 6/2006 | Latham et al. |
| 7,163,793 B2 | 1/2007 | Kudlicki et al. |
| 7,214,484 B2 | 5/2007 | Weber et al. |
| 7,964,350 B1 | 6/2011 | Fekete et al. |
| 8,211,637 B2 | 7/2012 | Kore et al. |
| 8,288,106 B2 | 10/2012 | Fekete et al. |
| 9,611,497 B2 * | 4/2017 | Pasloske ............ C12N 15/1003 |
| 2001/0049133 A1 | 12/2001 | McCabe et al. |
| 2002/0026046 A1 | 2/2002 | Pasloske et al. |
| 2002/0172972 A1 | 11/2002 | Tabor et al. |
| 2002/0177139 A1 | 11/2002 | Greenfield et al. |
| 2003/0170617 A1 | 9/2003 | Pasloske |
| 2004/0038213 A1 | 2/2004 | Kwon |
| 2004/0115658 A1 | 6/2004 | Weber et al. |
| 2005/0009045 A1 | 1/2005 | Greenfield et al. |

(Continued)

FOREIGN PATENT DOCUMENTS

EP  0261956  3/1988
EP  0410411  1/1991

(Continued)

OTHER PUBLICATIONS

Schaller et al. Molecular Microbiology (1998) 29: 605-615. (Year: 1998).*
Eun, H-M. "Chapter 3: Nucleases." Enzymology Primer for Recombinant DNA Technology. San Diego, CA: Academic Press, 1996. pp. 145-159.*
Ambion, "Cells-to-cDNA™ II", *Catalog No. 1722, 1723, Instruction Manual*, Apr. 2001, 1-15.
Ambion, "Cells-to-cDNA™ II: Reverse Transcription Kit", web.archive.org/web/2002042405181/http://ambion.com/catalog/ProdGrp.html Apr. 24, 2002, 1-3.
Ambion, "Cells-to-cDNA™ II: Reverse Transcription without RNA Isolation" *Catalog No. 1722, 1723, Protocol*, Mar. 2001, 1-10.
Ambion, "Online Catalog Dec. 12, 2010-Jan. 19, 2011" *Cells-to-cDNA II,Reverse Transcription Kit*, 1-2.
Ambion, "photograph, web.archive.org/web/20020603123018/http://ambion.com/news/", Jun. 3, 2002, 1.

(Continued)

*Primary Examiner* — Angela M. Bertagna

(57) ABSTRACT

The invention relates to methods for the detection of a specific sequence of RNA in a cell or tissue sample. The invention also relates to methods to enzymatically manipulate the RNA in a crude cell lysate in a number of applications.

18 Claims, 4 Drawing Sheets

(56) References Cited

U.S. PATENT DOCUMENTS

| | | | |
|---|---|---|---|
| 2005/0014169 | A1 | 1/2005 | Latham et al. |
| 2005/0069953 | A1 | 3/2005 | Fang et al. |
| 2005/0158783 | A1 | 7/2005 | Simms |
| 2005/0277121 | A1 | 12/2005 | Pasloske et al. |
| 2006/0068480 | A1 | 3/2006 | Christophers et al. |
| 2006/0115844 | A1 | 6/2006 | Finkelstein et al. |
| 2006/0148006 | A1 | 7/2006 | Fang et al. |
| 2006/0188892 | A1 | 8/2006 | Latham et al. |
| 2006/0269536 | A1 | 11/2006 | Deperthes et al. |
| 2007/0032418 | A1 | 2/2007 | Shapiro et al. |
| 2010/0159482 | A1 | 6/2010 | Kore et al. |
| 2013/0004941 | A1 | 1/2013 | Kore et al. |

FOREIGN PATENT DOCUMENTS

| | | |
|---|---|---|
| EP | 1044984 | 10/2000 |
| EP | 1476573 | 1/2010 |
| EP | 2367954 | 9/2011 |
| WO | 1992/008807 | 5/1992 |
| WO | 1993/015228 | 8/1993 |
| WO | 1994/026867 | 11/1994 |
| WO | 1995/020979 | 8/1995 |
| WO | 1996/000228 | 1/1996 |
| WO | 1999/025815 | 5/1999 |
| WO | 2000/017320 | 3/2000 |
| WO | 2000/017390 | 3/2000 |
| WO | 2001/021830 | 3/2001 |
| WO | 2001/042507 | 6/2001 |
| WO | 2003/002716 | 1/2003 |
| WO | 2003/064605 | 7/2003 |
| WO | 2010/071833 | 6/2010 |

OTHER PUBLICATIONS

Ambion, "Press Release", web.archive.org/web/200206031230/http://ambion.com/news, 2002.
Applied Biosystems, "TaqMan MicroRNA Cells to CT Kit", Product Bulletin, Nov. 2007, 1-4.
Applied Biosystems, "Testing of beta-formulation of Cells-to-cDNA III", Powerpoint presentation to Glaxo Smith Kline, Aug. 3, 2006, 1-20.
Barbacci et al., "Variant Hepatocyte Nuclear Factor 1 is required for visceral endoderm specification", *Development*, vol. 126, No. 21, Nov. 1999, 4795-4805.
Baum et al., "Regulation of expression of cytochrome P-450 2D mRNA in rat brain with steroid hormones", *Brain Research*, vol. 765, No. 1, Aug. 1997, 67-73.
Betzel et al., "Active-site geometry of proteinase K", *FEBS Letters*, vol. 197, Nos. 1-2, Mar. 3, 1986, 105-11.
Brady et al., "Construction of cDNA Libraries from Single Cells" *Methods in Enzymology*, vol. 225, 1993, 611-623.
Busche et al., "Expression of Angiotensin AT1 and AT2 Receptors in Adult Rat Cardiomyocytes after Myocardial Infarction: A Single-Cell Reverse Transcriptase-Polymerase Chain Reaction Study", *American Journal of Pathology*, vol. 157, No. 2, Aug. 2000, 605-611.
Dhamne et al., "The chloromethylketone protease inhibitor AAPF(CMK) also targets ATP-dependent helicases and SAP-domain proteins", *Journal of Cellular Biochemistry*, vol. 100, No. 3, Feb. 2007, 716-726.
Dziennis et al., "Cytokine Suppression of Dopamine-β-hydroxylase by Extracellular Signal-regulated Kinase-dependent regulated Kinase-dependent and -independent Pathways" *The Journal of Biological Chemistry*, vol. 278, No. 18, May 2, 2003, 15897-15904.
Edmands et al., "Rapid RT-PCR amplification from limited cell numbers" *Genome Research*, vol. 3, No. 6, Jun. 1994, 317-319.
Elbashir et al., "Analysis of Gene Function in Somatic Mammalian Cells Using Small interfering RNAs", *Methods*, vol. 26, No. 2, Feb. 1, 2002, 199-213.

EP03710760.4, EPO Communication Decision to grant a European patent pursuant to Article 971(1) EPC dated Dec. 10, 2009.
EP03710760.4, Opponent Letter faxed Dec. 6, 2011, 1-3.
EP03710760.4, Communication to the parties concerning termination of opposition proceedings mailed Jun. 21, 2012, 1-3.
EP03710760.4, Decision on Oral Proceedings mailed Mar. 5, 2012, 1-10.
EP03710760.4, Communication under Rule 71(3) EPC mailed Aug. 18, 2009, 1-6.
EP03710760.4, European Search Report dated Nov. 3, 2005.
EP03710760.4, Konig Szynka Tilmann von Renesse Response to Life Technologies Response dated Dec. 29, 2011 mailed, Jan. 9, 2012, 1-17.
EP03710760.4, Life Technologies Corporation's Comments faxed Dec. 29, 2011, 1-18.
EP03710760.4, Minutes of Oral Proceedings mailed Mar. 5, 2012, 1-15.
EP03710760.4, Notice of Opposition by BloMerieux dated Oct. 13, 2010, 1-39.
EP03710760.4,Notice of Opposition filed by Konig Szynka Tilmann von Renesse dated Oct. 19, 2010, 1-41.
EP03710760.4, Response to Late Submission of Opponent 1 in Preparation for Oral Proceedings faxed Jan. 16, 2012, 1-46.
EP03710760.4,Summons to Attend Oral Proceedings with Preliminary non-binding opinion of the Opposition Division mailed Jul. 27, 2011, 1-11.
EP03710760.4, Termination of Opposition Proceedings with Revocation of Patent mailed Jun. 14, 2012, 1-2.
EP09180993.9, European Search Report dated Feb. 11, 2010, 1-4.
EP10182642.8, European Search Report dated Jan. 26, 2011, 1-7.
EP14197615.9, "European Search Report", dated Apr. 28, 2015, 1-5.
Fekete et al., "Applied Biosystems Streamlined, High-throughput Assessment of siRNA-mediated Gene Knockdown in 384-23II Plates by Performing qRT-PCT from Cell Lysates", Abstract, presentation to Merck, Mar. 2007, 1.
Fink et al., "Immunostaining and laser-assisted cell picking for mRNA analysis" *Laboratory Investigation*, vol. 80, No. 3, 2000, 327-333.
Fink et al., "Immunostaining for cell picking and real-time mRNA quantitation" *American Journal of Pathology*, vol. 157, No. 5, Nov. 2000, 1459-1466.
Fink et al., "Rat Porphobilinogen Deaminase Gene: A Pseudogene-Free Internal Standard for Laser-Assisted Cell Picking", *BioTechniques*, vol. 26, No. 3, Mar. 1999, 510-516.
Fink et al., "Real-time quantatitive RT-PCR after laser-assisted cell picking" *Nature Medicine*, vol. 4, No. 11, Nov. 1998, 1329-1333.
Fung et al., "PCR amplification of mRNA directly from a crude cell lystate prepared by thermophilic protease digestion", *Nucleic Acids Research*, vol. 19, No. 15, 1991, 4300.
Genechoice, "cDNA Direct from Cells RT Kit", pgcsci.com/genechoice/GeneChoice_18.html, Jan. 28, 2012, 1-2.
Goldenberger et al., "A simple "universal" DNA extraction procedure using SDS and proteinase K is compatible with direct PCR amplification", *PCR Methods and Applications*, vol. 4, 1995, 368-370.
Hayashi et al., "A simple single-tube procedure of PCR assay for the detection of hepatitis C virus RNA", *Research in Virology*, vol. 145, 1994, 123-128.
Inivitrogen, *Proteinase K (solution)*, RNA Grade, Catalog No. 25530-049, Apr. 27, 2001, 1-2.
Invitrogen, "CellsDirect™ One-Step qRT-PCR Kits: for one-step real-time quantitative RT-PCR from cell lysate" *Catalogs Nos. 11753-100, 11753-500, 11754-100, 11754-500*, User Manual, Version B, No. 25-0870, Aug. 16, 2006, 1-36.
Invitrogen, "SuperScript™ III Platinum® CellsDirect two-Step qRT-PCR Kit with SYBR® Green:", *For two-step real-time quantitative RT-PCR from cell lysate using SYBR® Green I flourescent dye*, Catalog Nos. 11738-060, and 11738-068, Version B, No. 25-0751, Instruction Manual, Nov. 12, 2004, 1-29.
Ivarsson et al., "Evaluation of the Effects of DNase Treatment on Signal Specificity in RT-PCR and in Situ RT-PCR", *BioTechniques*, vol. 25, No. 4, 1998, 630-638.

(56) References Cited

OTHER PUBLICATIONS

Jena et al., "Amplification of genes, single transcripts and cDNA libraries from one cell and direct sequence analysis of amplified products derived from one molecule" *Journal of Immunological Methods*, vol. 190, No. 2, Apr. 1996, 199-213.
Jiang et al., "A Rapid RT-PCR Method for Detection of Intact RNA in Formalin-Fixed Paraffin-Embedded Tissues", *Nucleic Acids Research*, vol. 23, No. 15, Jan. 1, 1995, 3071-3072.
Kawasaki, "Sample Preparation from Blood, Cells, and Other Fluids" *PCR Protocols: A Guide to Methods and Applications*, Chapter 18, 1990, 146-152.
Kher et al., "Direct in situ reverse transcriptase-polymerase chain reaction", *American Journal of Physiology*, vol. 281, No. 2, Aug. 2001, C726-C732.
Klebe et al., "RT-PCR Without RNA Isolation", *BioTechniques*, vol. 21, No. 6, 1996, 1094-1100.
Kobs, "Isolation of RNA from Plant, Yeast and Bacteria", *Promega Notes*, No. 68, 1998, 28 (1-4 pages).
Kore et al., "Synthesis and application of MeOSuc-Ala-Ala-Pro-Phe-CH2Cl as potent proteinase K inhibitor", *Bioorganic & Medicinal Chemistry Letters*, vol. 19, No. 5, Mar. 1, 2009, 1296-1300.
Kudla et al., "RNAediting in tobacco chloroplasts leads to theformation of thetranslatablepsbL mRNA by a C to U substitution within the iniitiation condon", *EMBO Journal*, vol. 11, No. 3, 1992, 1099-1103.
Martinez et al., "Non-radioactive localization of nucleic acids by directin situ PCR and in situ RT-PCR in paraffin-embedded sections", *Journal of Histochemistry and Cytochemistry*, vol. 43, No. 8, Aug. 1995, 739-747.
Mensink et al., "Quantitation of minimal residual disease in Philadelphia chromosome positive chronic myeloid leukaemia patients using real-time quantitative rT-PCR", *British Journal of Haematology*, vol. 102, No. 3, Aug. 1998, 768-774.
Navia et al., "Structure of human neutrophil elastase in complex with a peptide chloromethyl ketone inhibitor at 1.84-Å resolution", *Proceedings of the National Academy of Sciences*, vol. 86, 1989, 7-11.
New England Biolabs, Catalog, 1993-1994, 96.
O'Brien et al., "RT-PCR assay for detection of transcripts from very few cells using whole cell lysates", *BioTehniques*, vol. 16, No. 4, Apr. 1994, 586-588, 590.
O'Leary, "Reducing the Impact of Endogenous Ribonucleases on Reverse Transcription-PCR Assay Systems", *Clinical Chemistry*, vol. 45, No. 4, Apr. 1999, 449-450.
PCT/US2003/002439, International Preliminary Examination Report dated Nov. 4, 2004, 1-4.
PCT/US2003/002439, International Search Report dated Dec. 10, 2003, 1-2.
PCT/US2009/068819, International Preliminary Report on Patentability dated Jun. 30, 2011, 19.
PCT/US2009/068819, International Search Report and Written Opinion dated Mar. 30, 2010, 1-13.
Peet et al., "Synthesis of Peptidyl Fluoromethyl Ketones and Peptidyl Alpha-Keto Esters as Inhibitors of Porcine Pancreatic Elastase , Human Neutrophil Elastase, and Rat and Human Neutrophil Cathespin G", *Journal of Medicinal Chemistry*, vol. 33, No. 1, Jan. 1, 1990, 394-407.
Pereira et al., "The 2.2 a crystal structure of human chymase in complex with succinyl-ala-ala-pro-phe-chloromethylketon e: structural explanation for its dipeptidyl carboxypeptidase specificity", *Journal of Molecular Biology*, vol. 286, No. 1, Feb. 12, 1999, 163-173.
Phillips et al., "Antisense RNA Amplification: A Linear Amplifictaion Method for Analyzing the mRNA Population from Single Living Cells", *Methods*. vol. 10, No. 3, Dec. 1996, 283-288.
Powers et al., "Reaction of Serine Proteases with Halomethyl Ketones" *Methods in Enzymology*, vol. 46, 1977, 197-208.
Powers et al., "Specificity of Porcine Pancreatic Elastase, Human Leukocyte Elastase and Cathepsin G", *Biochimicia et Biosysica Acts*, vol. 485, 1977, 156-166.
Price et al., "Properties of Chromatographically Purified Bovine Pancreatic Deoxyribonuclease", *Journal of Biological Chemistry*, vol. 244, No. 4, Feb. 25, 1969, 917-923.
Promega, "Certificate Analysis: RQ1 RNase-Free DNase (Cat.# M6101)", *Part 9PIM610*, Jan. 2009, 1-2.
Promega, "RQ1 RNase-Free DNase", Technical Bulletin No. 518, Feb. 2000, 1-4.
Qiagen, "FastLane Kits—from Sample Direct to Result", Sample & Assay Technologies, Jan. 2007, 1-8.
Qiagen, "RNeasy Mini Handbook: RNeasy Mini Protocol for Isolation of Total RNA from Animal Tissues", Third Edition, Jun. 2001, 30-41.
Reilly et al., "The degradation of human lung elastin by neutrophil proteinases", *Biochimica et Biophysica Acta*, vol. 621, No. 1, Jan. 24, 1980, 147-157.
Roche, "Proteinase K", Version 3, Jan. 2003, 1-2.
Sellner et al., "Reverse transcripts inhibits Taq polymerase activity", *Nucleic Acids Research*, vol. 20, No. 7, 1992, 1487-1490.
Shi et al., "Direct reverse transcription-polymerase chain reaction from whole blood without RNA extraction", *Genetic Analysis: Biomolecular Engineering*, vol. 9, Nos. 5-6, Dec. 1992, 149-150.
Sigma-Aldrich, "Product Information: Proteinase K, Catalog No. P6556", 2003, 1-2.
Sigma-Aldrich, "Proteinase K from Tritirachium Album", *Product Information*, Product Nos. P6556, P5056, P5568, P8044, P2308 and P4850, Nov. 9, 1998, 1-2.
Simon et al., "Detection of Phosphatidylinositol Glycan Class A Gene Transcripts by RT in Situ PCR Hybridization: A Comparative Study Using Fluorescein, Texas Red, and Digoxigenn-11 dUTP for Color Detection", *Journal of Histochemistry and Cytochemistry*, vol. 45, No. 12, 1997, 1659-1664.
Specht et al., "Quantitative Gene Expression Analysis in Microdissected Archival Formalin-Fixed and Paraffin-Embedded Tumor Tissue", *American Journal of Pathology*, vol. 158, No. 2, Feb. 2001, 419-429.
Stahlberg et al., Properties of the Reverse Transcription Reactin in mRNA Quantification, Clin Chem., vol. 50, No. 3, 2004, 509-515.
Stein, "Catalysis by Human Leukocyte Elastase: Substrate Structural Dependence of Rate-Limiting Proteolytic Catalysis and Operation of the Charge Relay System", *Journal of the American Chemical Society*, vol. 105, No. 15, 1983, 5111-5116.
Stein et al., "Mechanism of Inactivation of Human Leukocyte Elastase by a Chloromethyl Ketone: Kinetic and Solvent Isotope Effect Studies", *Biochemistry*, vol. 25, No. 19, Sep. 1986, 5414-5419.
Stratagene, "SideStep QPCRcDNA Synthesis Kit", Instruction Manual, Catalog No. 400908, Revision B.01, 2007, 1-26.
Su et al., "High-throughput RT-PCT analysis of multiple transcripts using a microplate RNA isolation procedure", *BioTechniques*, vol. 22, No. 6, Jun. 1997, 1107-1113.
Sumida et al., "Evaluation of induction of CYP3A mRNA Using the HepG2 Cell Line and Reverse transcription—PCR", *Biological and Pharmaceutical Bulletin*, vol. 22, No. 1, Jan. 1999, 61-65.
Tang et al., "A polymerase chain reaction based method for detecting Mycoplasma/Acholeplasma contaminants in cell culture", *Journal of Microbiological Methods*, vol. 39, No. 2, Jan. 2003, 121-126.
TEL-Test, Inc., "RNA Stat-60", isotexdiagnostics.com/rna_stat-60_reagent.tml, cited in Baum et al., 1997, 1-4.
Tullis et al., "Calcium Protects DNase I from Proteinase K: A New Method for the Removal of Contaminaing RNase DNase I", *Analytical Biochemistry*, vol. 107, No. 1, Sep. 1980, 260-264.
Webster's, Third New International Dictionary, 1993, 1448.
Webster's, Third New International Dictionary, 1993, 28.
Webster's, Third New International Dictionary,1993, 641.
Wikipedia, "Lysis", http://www.en.wikipedia.org/wiki/Lysate, Definition, Feb. 28, 2011, 1-5.
Wolf et al., "Inhibition of Proteinase K By Methoxysuccinyl-Ala-Ala-Pro-Ala-Chlorom Ehtyl Ketone an X-ray Study at 2.2-A Resolution", *Journal of Biological Chemistry*, vol. 266, No. 26, 1991, 17695-17699.
Xu et al., "One-Step Analysis and Quantification of RNA by RT-PCR: Using High-Temperature Reverse Transcription", *Focus*, vol. 22, No. 1, 2000, 3-5.

(56) References Cited

OTHER PUBLICATIONS

Yan et al., "One-tube protocol for single-cell reverse transcriptase-polymerase chain reaction", *Analytical Biochemistry*, vol. 304, No. 2, May 15, 2002, 267-270.

* cited by examiner

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
gattgtcacc ataagcagc                                                    19

<210> SEQ ID NO 2
<211> LENGTH: 19

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
cccctgaatg cggctaatc                                                19

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
cggaaccgac tactttgggt gtccgt                                        26

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gaaggtgaag gtcggagt                                                 18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gaagatggtg atgggatttc                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
caagcttccc gttctcagcc                                               20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
tcacccacac tgtgcccatc tacga                                         25

<210> SEQ ID NO 8
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 8
cagcggaacc gctcattgcc aatgg                                          25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9 atgcccccccc catgccatcc tgcgt                                         25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ccatcgtgtc atcaaggact tcat                                           24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
cttgccatcc agccaggagg tctt                                           24

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tggcacagga ggaaagagca tctatg                                         26

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ctggccggtc atcaactga                                                 19

<210> SEQ ID NO 14
<211> LENGTH: 22
<212> TYPE: DNA
<213> ORGANISM: Artificial Sequence
```

```
<220> FEATURE:
<223> OTHER INFORMATION: Description of Artificial Sequence:  Synthetic
      Primer

<400> SEQUENCE: 14
acaagcaaac cgaaatctct gg                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
aatgcgtcct gagcagcagc cc                                              22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
ggcgcagtgc ttctctacag                                                 20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 17
tagggtctcg tcccgcttc                                                  19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 18
ttctccagac ccaccacacc gc                                              22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19
tcaagaacga aagtcggagg                                                 20

<210> SEQ ID NO 20
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      Primer

<400> SEQUENCE: 20
ggacatctaa gggcatcaca                                                  20

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
tggctgaacg ccacttgtcc ctctaa                                           26

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
cacgcatctt gttttcccaa t                                                21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ctcgagtgcg ttcgtgattt c                                                21

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
aattggcatc aaaacgcaaa caaatc                                           26
```

CRUDE BIOLOGICAL DERIVATIVES COMPETENT FOR NUCLEIC ACID DETECTION The present application claims priority to U.S. patent application Ser. No. 13/463,624 filed May 3, 2012, now U.S. Pat. No. 9,611,497, Apr. 4, 2017, which application is a continuation application of U.S. application Ser. No. 10/352,806 filed Jan. 28, 2003, now abandoned, which application claims the benefit of provisional U.S. Patent Application Ser. No. 60/352,402 filed Jan. 28, 2002. The entire texts of the above referenced applications are incorporated herein by reference and without disclaimer.

BACKGROUND OF THE INVENTION

1. Field of the Invention

The present invention relates generally to the field of RNA analysis, more specifically it teaches a more direct method for the detection of a specific sequence of RNA in a biological unit, for example a virus, cell or tissue sample. More generally, the invention may be used to enzymatically manipulate and protect the RNA in a crude cell lysate for a number of applications.

2. Description of Related Art

Reverse transcription followed by the polymerase chain reaction (RT-PCR) is one of the main methods used for measuring mRNA levels from a small number of cells. As well, reverse transcription is the first step in several strategies towards amplifying a small quantity of total or poly (A) RNA (U.S. Pat. No. 5,554,516; U.S. Pat. No. 5,891,636; Phillips, 1996). The amplified RNA can be used to probe arrays for monitoring the expression of multiple genes (Lockhart, 1996; U.S. Pat. No. 6,316,608). Prior to performing any of these methods, the substrate RNA is isolated from a biological sample, in most cases. Current procedures for RNA isolation involve numerous steps and are not very amenable to high throughout analysis.

In general, the techniques used for RNA isolation involve phenol-chloroform extraction (Mesink, 1998) or guanidinium lysis followed by adsorbing the RNA to a glass fiber filter (Su, 1997). By streamlining the RNA isolation step, the analysis of a large number of samples involving reverse transcription or some other enzymatic manipulation becomes much faster, simpler, and less expensive. Klebe et al. (1996) developed a strategy of creating a crude cell lysate by freeze-thawing cells at a concentration of 10 cells/µl in the presence of placental RNase inhibitor. The crude lysate, containing no more than 250 cells, was then used for reverse transcription to produce cDNA. This technology serves as the basis for the "cDNA Direct from Cells" kit sold by PCG (Cat. #62-613100). As pointed out by Klebe (1996), this method is limited in that the RNase inhibitor is only specific for RNase A. There are many other types of RNases in a cell that may contribute to RNA degradation and would not be inhibited by a single specific RNase inhibitor. Another problem is that some types of cells have a much higher concentration of RNase activity thereby making it more difficult to maintain the intactness of the RNA in a crude lysate (O'Leary, 1999). A similar protocol was used by Yan. (2002) to detect an mRNA from one cell by RT-PCR. However, it differed in that it also included a DNase treatment to remove genomic DNA and only 1 to 3 cells were used in the reactions.

Busche (2000) used a procedure similar to Klebe (1996) to reverse transcribe RNA from a few cells. Ten myocyte section profiles from various samples were selected by laser-assisted picking, transferred into 10 µl of first strand buffer containing 4% ribonuclease inhibitor, cooled on ice for 5 minutes and snap frozen. The samples were incubated 70° C. for 10 minutes and cooled on ice for 5 minutes. Reverse transcription was performed in a total of 17.5 µl using 5 µl of the sample and an MMLV-RT, and incubated 20° C. for 10 minutes followed by 43° C. for 60 minutes. The cDNA was subsequently used for PCR.

Brady (1993) generated cDNA from a few cells for creating cDNA banks using lysed cells. One to 40 cells in less than 0.5 µl volume are added to 4 µl of first-strand buffer and stored on ice for less than one hour before reverse transcription. The first strand buffer contains 0.5% Nonidet P-40 (NP-40) to lyse the cellular membrane and an RNase inhibitor to protect the RNA from degradation. The NP-40 does not lyse the nuclear membrane and therefore, the nucleus can be pelted by centrifugation (e.g., centrifugation at 12,000×g, 4° C., for 50 seconds), to deplete the cell lysate of genomic DNA if desired. The cytoplasmic RNA is used for reverse transcription. The cell lysate in the first strand buffer is incubated at 65° C. for 1 minute to unfold the mRNA. The reaction is cooled to room temperature for 3 minutes to anneal the oligo (dT) primer. One µl of a 1:1 mix of MMLV-RT and AMV-RT is added to the reaction and incubated 15 minutes at 37° C. The reaction was stopped by heating to 65° C. for 10 minutes. This procedure does not involve any protease treatment, any DNase treatment and is only recommended for no more than 40 cells.

A kit called ExpressDirect™ (Pierce Chemical Company, Cat. #20146), isolates poly(A) RNA directly from a cell lysate. The wells of a 96-well plate have oligo dT immobilized to them. Cells are lysed in the wells and the poly(A) RNA hybridizes to the oligo dT. After hybridization, the cell lysates are removed and the wells washed to remove cell debris. The poly(A) RNA may then be eluted from the well and then reverse transcribed. Alternatively, the poly(A) RNA could be reverse transcribed directly in the 96-well plate. The immobilized oligo dT serves as the primer.

Protocols exist for the detection of bacterial DNA sequences from tissue culture in order to assay for *Mycoplasma* contamination (U.S. Pat. No. 5,693,467; and Tang, 2000). This procedure involves incubating the cells from tissue culture with proteinase K. However, there is no mention of using this procedure to synthesize cDNA. In the *Mycoplasma* Detection kit from the American Type Culture Collection (Cat. #90-1001K) cells to be tested for *Mycoplasma* from tissue culture can be subjected directly to PCR if the *Mycoplasma* contamination is suspected to be severe. However, to achieve maximum sensitivity the cells are incubated in a lysis buffer (1×PCR buffer, 0.5% NP-40, 0.5% Tween 20) with proteinase K (18 µg/ml) at 60° C. for one hour. The lysate is then incubated at 95° C. for 10 minutes to inactivate the proteinase K. The manual states that the DNA extract may be used directly as the template for PCR without further purification. However, it cautions that the completion of the secondary DNA extraction procedure facilitates removal of all possible PCR inhibitors. The secondary extraction protocol involves adding 500 µl water, mixing well, adding 600 µl isopropanol and 1 µl glycogen (20 mg/ml), mixing well, incubating at −20° C. for at least 30 minutes, centrifuging to pellet the DNA and then removing the supernatant. The DNA pellet is washed with 75% ethanol, centrifuged again and the supernatant removed. No mention is made in that this procedure can be used to prepare RNA for reverse transcription.

Fink (2000a; 2000b) used a proteinase K treatment to increase the efficiency of RT-PCR from cells isolated by laser-assisted cell picking. Between 15 and 20 frozen or fixed cells were selected by laser-assisted cell picking, harvested by a syringe needle, added to 10 μl of first-strand-buffer and frozen in liquid nitrogen. After thawing the cells, proteinase K was added to the sample to 100 μg/ml, the sample was incubated at 53° C. for 30 minutes and then heated at 99° C. for 7 minutes to denature the proteinase K and RNA. Reverse transcription was performed directly on the sample using murine maloney leukemia virus-reverse transcriptase (MMLV-RT), at 20° C. for 10 minutes and 43° C. for 60 minutes. The cDNA from this reaction was used for PCR. In both of these publications, the fixed cells were frozen before the proteinase K treatment, the concentration of cells was no more than 2 cells/μl and no DNase treatment was used to remove genomic DNA.

Cells to cDNA™ (Ambion, Inc., #1712 & 1713; U.S. patent application Ser. Nos. 09/160,284 and 09/815,577, the entire disclosures of which are incorporated herein by reference) is a kit where there is no RNA isolation step. A crude cell lysate is prepared containing total RNA. Cells from tissue culture are washed once in PBS and then resuspended in Cell Lysis Buffer. The cells are incubated at 75° C. for 5 minutes, having two important effects. First, the cell membranes are lysed, thereby releasing the RNA into the Cell Lysis Buffer. As well, the heating step inactivates the endogenous RNases, thus protecting the RNA from degradation. A key component in the Cell Lysis Buffer is a reducing agent such as dithiothreitol (DTT). It was discovered that RNases can be inactivated by heating them in the presence of reducing agents (U.S. patent application Ser. Nos. 09/160, 284 and 09/815,577). Following cell lysis, the crude cell lysate is incubated with DNase I to degrade the genomic DNA. After the DNase I is inactivated by a heating step, the cell lysate is ready for reverse transcription and then PCR. The Cells-to-cDNA™ kit (Ambion, Inc. Cat. #1712 & 1713) is adapted for use with samples having low cell concentrations. If higher cell concentrations are used, then RNA quantification can cease to be linear and in some cases, the signal can be completely inhibited. It appears that the reverse transcriptase can be inhibited by the higher cell concentrations. In general, the maximum optimal cell concentration the Cells-to-cDNA™ kits is 100 to 200 cells per μl in the Cell Lysis Buffer.

A procedure that enables the direct use of a cell lysate at a higher cell concentration would have many more applications and provide a greater dynamic range for quantification, thereby complimenting the technology in Cells-to-cDNA. Also, because of the issue of higher cell concentrations, Cells-to-cDNA is most useful in the context of cells from tissue culture. As well, methods that are more useful in the direct use of a tissue in a reverse transcription reaction would decrease the time and the amount of handling required to prepare a sample for reverse transcription or other enzymatic applications.

SUMMARY OF THE INVENTION

The above-described deficiencies in the art are overcome by the present invention.

Broadly, the present invention relates to methods comprising: obtaining at least one biological unit containing RNA; obtaining at least one catabolic enzyme; preparing an admixture of the biological unit and the catabolic enzyme; and incubating the admixture under conditions where the catabolic enzyme is active.

The term "biological unit" is defined to mean any cell or virus that contains genetic material. In most aspects of the invention, the genetic material of the biological unit will include RNA. In some embodiments, the biological unit is a prokaryotic or eukaryotic cell, for example a bacterial, fungal, plant, protist, animal, invertebrate, vertebrate, mammalian, rodent, mouse, rat, hamster, primate, or human cell. Such cells may be obtained from any source possible, as will be understood by those of skill in the art. For example, a prokaryotic or eukaryotic cell culture. The biological unit may also be obtained from a sample from a subject or the environment. The subject may be an animal, including a human. The biological unit may also be from a tissue sample or body fluid, e.g., whole blood, plasma, serum, urine or cerebral spinal fluid.

The catabolic enzyme can be any catabolic enzyme known to those of skill in the art as of the filing of this specification or at anytime thereafter. In some preferred embodiments, the catabolic enzyme is a protease, for example, proteinase K. In other embodiments, the catabolic enzyme degrades carbohydrates, for example, amylase or cellulase. In some embodiments, the catabolic enzyme degrades lipids, such as lipase. In other embodiments the catabolic enzyme degrades DNA, such as, for example, bovine pancreatic DNase I. Of course, the various embodiments of the invention may comprise the use of one, two, three, four, five, six, seven, or more different catabolic enzymes, in order to achieve the desired goals of a given method. In some embodiments, any enzymes that digest DNA, lipids, fats, carbohydrates, connective tissue or any other molecules, proteins, or biological compounds that inhibit enzymatic reactions, specifically reverse transcription or PCR are contemplated. In certain embodiments, a catabolic enzyme may or may not be included in the Cell Lysis Buffer and in some case may be introduced before, after or simultaneously with the Cell Lysis Buffer. For example, it is entirely possible, in RT-PCR embodiments of the invention, to use both proteinase K to destroy RNase in a cellular extract in combination with one or more other catabolic enzymes to degrade other portions of the cellular extract to the benefit of the reaction. Of course, in such cases, it may be necessary to balance the concentrations and/or timing of the addition of the various catabolic enzymes, in order to prevent, for example, the degradation of a cellulase by a proteinase. However, such balancing will be well within the skill of one of skill in the art, in view of this specification. Proteases that may be used in the methods of the invention include, but are not limited to, Serine proteases that include but are not limited to Trypsin, Chymotrypsin, Elastase, Subtilisin, Streptogrisin, Thermitase, Aqualysin, and carboxypeptidase A, D, C, or Y; cysteine proteases that include but are not limited to Papain and Clostripain; acid proteases that include but are not limited to Pepsin, Chymosin, and Cathepsin; metalloproteases that include but are not limited to Pronase, Thermolysin, Collagenase, Dispase; and various aminopeptidases and Carboxypeptidase A, B, E/H, M, T, or U. In some embodiments of the invention, these proteases could be used in place of proteinase K. It is possible that a mixture of proteases could be used instead of a single protease to generate a cell lysate compatible with reverse transcription and PCR.

In certain embodiments, a protease and a DNase enzyme may be administered simultaneously or in the same reactions. This simultaneous treatment using proteases and DNase enzymes is an unexpected and novel finding, as described below. In some embodiments, 1, 2, 3, 4, 5, 6, 7, or more catabolic enzymes may be included in a protease/DNase composition or reaction. For example, multiple proteases or co-proteases may be included with lipases, collagenases, nucleases, and virtually any other enzyme that may be used to remove inhibitors of a reaction, e.g., polymerization reactions.

In some aspects of the invention, preparing an admixture of the biological unit and the catabolic enzyme is further defined as comprising preparing an extract of the biological unit and preparing an admixture of the extract of the biological unit and the catabolic enzyme. Further, preparing an admixture of the extract of the biological unit and the catabolic enzyme may comprise: first preparing the extract; and then mixing the extract with the catabolic enzyme. Alternatively, preparing an admixture of the extract of the biological unit and the catabolic enzyme could comprise: first mixing the biological unit and the catabolic enzyme; and then preparing the extract from the biological unit in the presence of the catabolic enzyme.

In some preferred embodiments, the invention relates to methods for producing cDNA from one or more biological units, possibly different types of biological units. In some embodiments, any enzyme that can utilize a nucleic acid or in particular RNA as template or substrate is contemplated. In certain embodiments, an admixture may be incubated with a nucleic acid polymerase. In some embodiments, the nucleic acid polymerase is a ribonucleotide polymerase, e.g., bacterial or viral RNA polymerase. Preferred embodiments may further comprise incubating the admixture with reverse transcriptase under conditions to allow reverse transcription. Typically, the methods will further comprise amplifying the products of the reverse transcription, and these methods may further comprise incubating said admixture with a deoxyribonuclease prior to the reverse transcription reaction. In some preferred embodiments the catabolic enzyme is a protease that is capable of inactivating ribonucleases in the admixture. For example, the protease may be proteinase K.

These embodiments have certain benefits in the context of RT-PCR, with regard to the issues described above. In such methods, a freezing step is not required. Further, the admixture may contain 1, 5, 10, 100, 200, 300, 400, 500, 1,000, 2,000, 3,000, 4,000, 5,000, 10,000, or 15,000 or more cells/µl, as well as any concentration of cells between any two of these concentrations. Note that these concentration are for typical eukaryotic cells. Since prokaryotic cells are typically a thousand times smaller these concentration may be adjusted accordingly. Typically, it is the reverse transcriptase enzyme that is inhibited by the higher cell concentrations of cell lysate. In certain embodiments, the upper limit of cell concentration may be increased by either using other catabolic enzymes or other methods or compositions to destroy the inhibitors of the RT or by using RTs that are less inhibited by the lysates. In addition, DNase I treatment can be included although this is not necessary in all embodiments, for example, if the PCR primers are designed properly and the gene structure is amenable. In view of these improvements, the methods of the invention are well-suited to the analysis of a large number of differentially treated samples grown in tissue culture. For example, the regulation of an mRNA may be followed as cells are treated with increasing concentrations of a particular chemical (Sumida, 1999). Alternatively, cells may be treated with a panel of different drugs to screen for candidates that have the desired effect on a particular mRNA or a time course may be followed (Su, 1997).

Some embodiments of the invention further comprise adding an RNase inhibitor to the admixture, in addition to any proteinase that inhibits or degrades RNase. For example, the RNase inhibitor is a non-proteinaceous RNase inhibitor, such as ADP or a vanadyl complex. Proteinaceous inhibitors could also be used such as placental ribonuclease inhibitor or antibodies that inactivate specific ribonucleases.

In some embodiments, the final concentration of the catabolic enzyme added is between about 0.00001, 0.0001, 0.001, 0.01, 0.1, 1, 2, 3, 4, 5, 10, 15, 20, or 25 mg/ml, as well as any concentration between any two of these concentrations. In some embodiments, the final concentration of the catabolic enzyme added is between about 0.00001, 0.0001, 0.001, 0.01, 0.1, 1, 2, 3, 4, 5, 10, 15, 20, or 25 mg/ml, as well as any concentration between any two of these concentrations in the admixture, more preferably, between 0.001 and 2 mg/ml, and even more preferably, between 0.025 and 1 mg/ml.

Typically, the catabolic enzyme is comprised in a buffer composition prior to admixing.

In some preferred embodiments, the admixture is incubated at between 0° C. and 75° C. However, this temperature may vary during the course of the procedure. In certain embodiments, the admixture may be incubated at between 0° C. and 100° C. Further, it is entirely possible to raise the temperature to a point where the catabolic enzyme is ultimately inactivated. For example, proteinase K tends to be inactivated at around 75° C. The inventors frequently place proteinase K containing reactions in a water bath at 75° C., knowing that when the reaction reaches this temperature, the enzyme activity will be destroyed, but that the benefit of the enzyme in destroying RNase will be achieved by that point.

In preferred embodiments, the invention is related to methods for producing cDNA from one or more biological units comprising: obtaining at least one biological unit; obtaining at least one catabolic enzyme; preparing an admixture of the biological unit and the catabolic enzyme; incubating the admixture at a temperature where the catabolic enzyme is active; and incubating with reverse transcriptase under conditions to allow reverse transcription. The components of this reaction can be any of the components described above.

Other embodiments of the invention relate to kits for producing cDNA from a biological unit, comprising, in a suitable container: a buffer; and a catabolic enzyme. In some such kits, the buffer and the catabolic enzyme are comprised in the same container. The kits may further comprise a reverse transcription buffer, a reverse transcriptase, and dNTP mix. The kits may additionally contain a deoxyribonuclease. In some preferred embodiments, the catabolic enzyme is proteinase K. The kits may further comprise an RNase inhibitor.

In some preferred embodiments, the kits for producing cDNA from a biological unit comprises, in one or more suitable container(s): a biological unit lysis buffer; a deoxyribonuclease; an RNase inhibitor; a reverse transcription buffer; reverse transcriptase; dNTPs; and an Armored RNA® control. "Armored RNA" is a an Ambion trademark for ribonuclease resistant RNA particles produced according to the methods disclosed in U.S. Pat. Nos. 6,399,307; 6,214,982; 5,939,262; 5,919,625; and 5,677124, the entire contents of which are incorporated herein by reference. These kits may further comprise a protease inhibitor, such as phenylmethylsulfonyl fluoride (PMSF), and/or a thermostable DNA polymerase.

Kits suitable for the practice of the methods described herein are sold by Ambion under the trademark Cells-to-cDNA II™.

In other aspects of the invention, a Cell Lysis Buffer comprising a catabolic enzyme, 1 mM $CaCl_2$, 3 mM $MgCl_2$, 1 mM EDTA, 1% Triton X100, and 10 mM Tris pH 7.5 is contemplated. In certain embodiments, the catabolic enzyme is Proteinase K. In some embodiments, Proteinase K may is present at a concentration of about 0.2 mg/ml.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
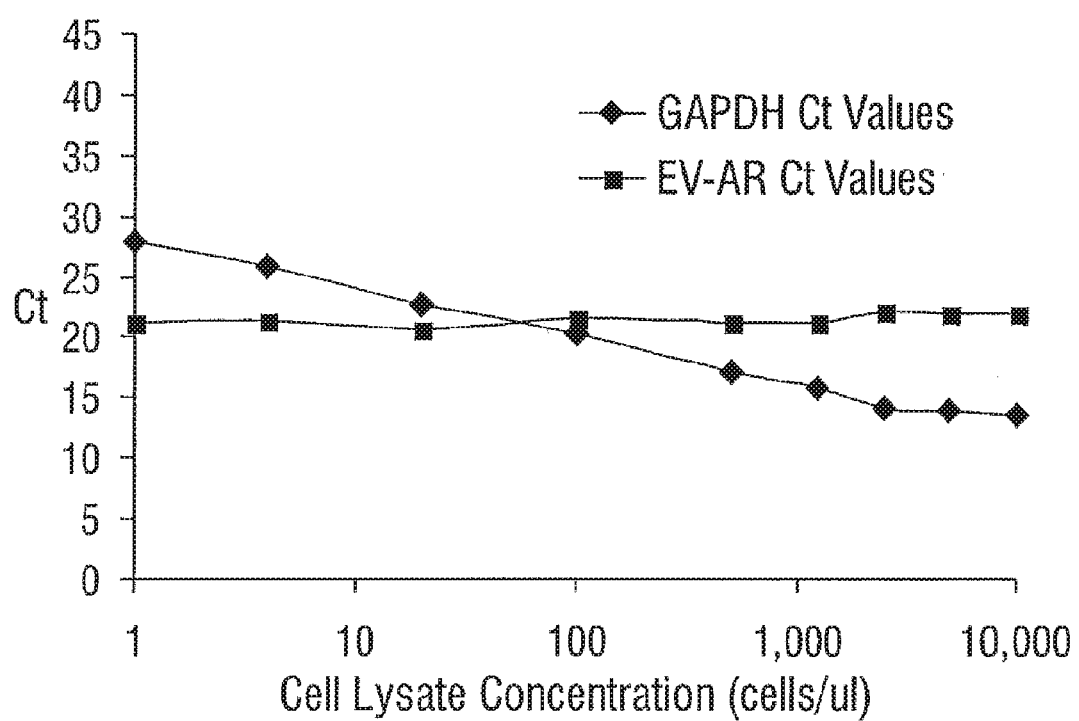
FIG. 1. Illustrates an example of measuring the levels of GAPDH mRNA and the enterovirus Armored RNA® by real-time RT-PCR in the ABI 7700 in different concentrations of HeLa cells. The cells were processed using the methods of the invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

A Basic Procedure for Cells Derived from Tissue Culture

HeLa cells are used as an exemplary cell type of cells that are suitable for treatment using the compositions and methods described herein. However, the invention is in no way limited to the exemplary cell type. It is expected that the compositions and methods apply to all cell types. One of ordinary skill would, in light of the disclosure, expect all other cells types to be amenable to the methods of the present invention.

To demonstrate the basic methods for cells derived from tissue culture, HeLa cells were grown in Dulbecco's Modified Eagle Medium with 10% fetal bovine serum in a tissue culture flask to 50 to 75% confluency. The medium was removed and then the cells were incubated with trypsin (0.05% trypsin, 0.53 mM EDTA) for 10 minutes at 37° C. Trypsin was inactivated by re-suspending the cells in medium with 10% fetal bovine serum. Cell concentration was determined with a hemacytometer and then the volume, calculated to contain 6 million cells, was centrifuged at 3,000 rpm for 5 minutes. The medium was removed and the cells were washed once with 1 ml of cold phosphate buffered saline (PBS). The cells were resuspended in 30 µl of PBS and dilutions were made in PBS using the stock solution of 200,000; 100,000; 50,000; 25,000; 10,000; 2,000; 400; 80; and 20 cells/µl. Five µl of each dilution were added to 95 µl of Cell Lysis Buffer [0.2 mg/ml proteinase K (Ambion, Inc., #2546), 1 mM $CaCl_2$, 3 mM $MgCl_2$, 1 mM EDTA, 1% Triton X100, 10 mM Tris pH 7.5] such that the final cell concentrations were 10,000; 5,000; 2,500; 1,250; 500; 100; 20; 4 and 1 cells/µl. Two µl of the enterovirus Armored RNA® control (Ambion RNA Diagnostics, #42050; Pasloske, 1998) may be included in the Cell Lysis Buffer as a positive control to a final concentration of ~40,000 copies/µl. The EV Armored RNA® Primer and probe sequences were as follows: Forward 5'-GATTGTCAC-CATAAGCAGC-3' (SEQ ID NO. 1); Reverse 5'-CCCCT-GAATGCGGCTAATC-3' (SEQ ID NO. 2); TaqMan Probe: 5'-(FAM)-CGGAACCGACTACTTTGGGTGTCCGT-(TAMRA)-3' (SEQ ID NO. 3). The samples were incubated at 75° C. for 10 minutes and then cooled to 37° C. DNase I (Ambion, Inc., #2222) was added to the cell lysate to a concentration of 0.02 to 0.04 U/µl, incubated at 37° C. for 15 to 30 minutes and then incubated at 75° C. for 5 minutes to inactivate the DNase I. The cell lysate is now compatible for reverse transcription and PCR.

Reverse Transcription Followed by PCR

Five µl of the cell lysate from above was added to 2 µl of random primers, 4 µl dNTP mix (2.5 mM each) and 5 µl of RNase-free water (Ambion, Inc., #9932). The mixture was incubated at 75° C. for 3 minutes and cooled to room temperature. Two µl 10×RT buffer (500 mM Tris pH 8.3, 750 mM KCl, 30 mM $MgCl_2$, 50 mM DTT), 1 µl (10 U/µl) of placental RNase Inhibitor (#2687, Ambion, Inc.), and 1 µl of MMLV-RT (25 U/µl) were added and the reaction was incubated at 42° C. from 15 minutes to 60 minutes to synthesize cDNA. Negative control reactions were included that do not include MMLV-RT to assess the level of genomic DNA contamination. Reactions that do not include MMLV-RT should not generate any detectable signal during PCR. The reverse transcription reaction was incubated at 92° C. for 10 minutes to inactivate the MMLV-RT.

For PCR, 5 µl of the cDNA were combined with 1 unit of SuperTaq Polymerase (Ambion, Inc.), 2.5 µl 10×PCR buffer (100 mM Tris-Cl pH 8.3, 500 mM KCl, 8% glycerol, 0.1% Tween 20), 2 µl dNTP mix (2.5 mM each), 3 µl 25 mM $MgCl_2$, 1 µl of the primer pair (10 µM mixture of the forward and reverse primers) and 1 µl of the TaqMan® probe (2 µM), 0.5 µl 50×ROX Standard, 8.8 µl RNase-free water (Ambion, Inc.). Human GAPDH Primer and probe sequences were employed as follows: Forward: 5'-GAAGGTGAAGGTCG-GAGT-3' (SEQ ID NO. 4); Reverse: 5'-GAAGATGGT-GATGGGATTTC-3' (SEQ ID NO. 5); TaqMan Probe: 5'-(FAM)-CAAGCTTCCCGTTCTCAGCC-(TAMRA)-3' (SEQ ID NO. 6). The reactions were placed in an ABI 7700 Prism thermocycler and ran using following profile: 94° C., 2 minutes; [94° C., 20 seconds; 60° C., 20 seconds]×40 cycles.

GAPDH was detectable in all samples that included HeLa cells. A plot of the threshold cycle (Ct value) against cell concentration was linear up to 2,500 cells/µl. GAPDH signal was readily detected at cell concentrations greater than 2,500 cells/µl but a slight inhibition of the reactions was observed. FIG. 1. In addition, the Ct value for the enterovirus Armored RNA® was unchanged in all of the cell concentrations up to 2,500 cells/µl indicating that there was no inhibition of the reverse transcriptase or PCR up to 2,500 cells/µl, which was in agreement with the GAPDH data. FIG. 1.

The cDNA synthesis reactions that did not include MMLV-RT (MMLV-RT minus control) did not generate any signal in the amplification reaction, demonstrating that genomic DNA was degraded to undetectable levels and that signals produced by RT-PCR were attributable solely to the amplification of the cDNA.

Example II

The Invention Functions with Multiple Cell Lines

In order to show the applicability of the invention across cell types HeLa S3, MCF-7, COS-7, CHO-K1, and J558 cells were grown to 50-75% confluency in appropriate growth media. The cells were harvested by trypsin, re-suspended in growth medium and counted with a hemacy-tometer. Two million of each cell type were collected and the cells were pelleted by centrifugation (3,000 rpm for 5 minutes). The cells were washed with 1×PBS (Ambion, Inc.) and pelleted again by centrifugation (3,000 rpm for 5 minutes). The cells were resuspended in 40 µl 1×PBS and four 1:5 dilutions were made in PBS. Five µl of each cell suspension was added to 95 µl Cell Lysis Buffer for final cell concentrations of 2,500; 500; 100; 20; and 4 cells/µl in the Cell Lysis Buffer. The cells were lysed, DNase I treated, and reverse transcribed followed by PCR as in EXAMPLE I.

In each cell line, β-actin mRNA was detected by real-time PCR at each cell concentration. β-actin primer and probe sequences were employed as follows: Forward: 5'-TCAC-CCACACTGTGCCCATCTACGA-3' (SEQ ID NO. 7); Reverse: 5'-CAGCGGAACCGCTCATTGCCAATGG-3' (SEQ ID NO. 8); TaqMan Probe: 5'-(FAM)-ATGCCC-X (TAMRA)-CCCCCATGCCATCCTGCGTp-3' (SEQ ID NO. 9) where X indicates a linker-arm nucleotide, and p indicates phosphorylation. The cDNA synthesis reactions that did not include MMLV-RT (MMLV-RT minus control) did not generate any signal in the amplification reaction proving that the genomic DNA was degraded to undetectable levels and that signals produced by RT-PCR were attributable solely to the amplification of the cDNA in each cell line.

Example III

Use of Methods on Fixed Cells from Tissue Culture

To demonstrate the methods of the invention on fixed cells from tissue culture, HeLa S3 cells were grown to 75% confluency in Dulbecco's Modified Eagle Medium with 10% fetal bovine serum. The cells were harvested as described in EXAMPLE I. Approximately 6 million cells were collected and pelted (3,000 rpm for 5 minutes). The cells were re-suspended in 0.5 ml of 1×PBS. A volume of 0.5 ml of a solution containing 2% formalin in PBS was added to make a final concentration of 1% formalin. The cells were vortexed and placed at 4° C. for 1 hour. Subsequently, the cells were formalin fixed.

The cells were pelleted to remove the formalin. The cells were resuspended in PBS and washed again to remove trace amounts of formalin. The cells were re-suspended in 120 µl PBS and four 1:5 dilutions were made. Five µl of each cell suspension was added to 95 µl cells lysis buffer for a final cell concentration of 2,500; 500; 100; 20 and 4 cells/µl. The same procedure was performed for cells that were not formalin fixed. The cells were lysed, DNase I treated, reverse transcribed and followed by PCR as in EXAMPLE I.

Figure 2:
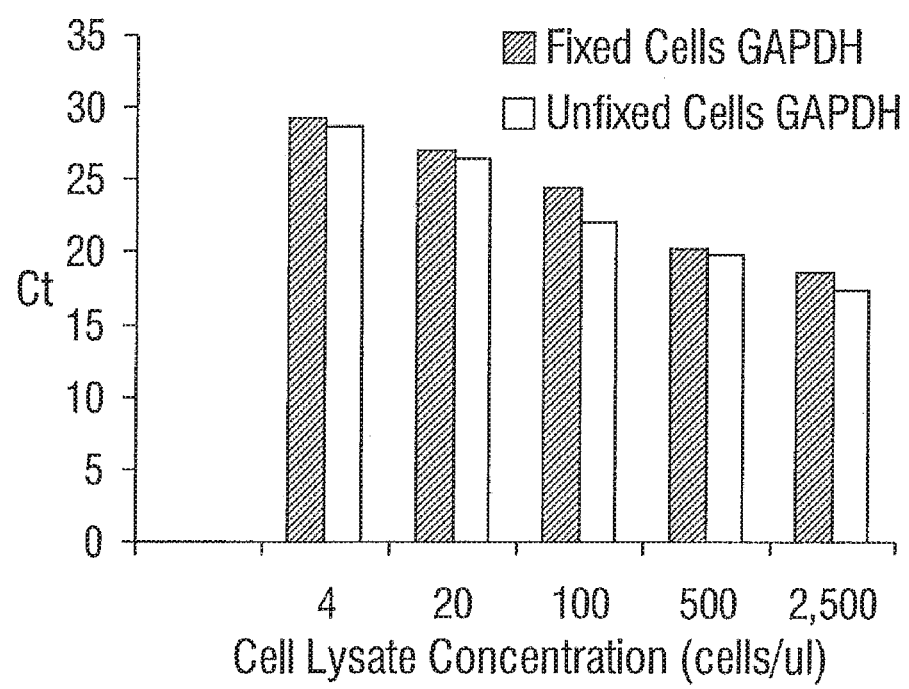
FIG. 2. Illustrates an example of measuring the levels of GAPDH mRNA by real-time RT-PCR in the ABI 7700 in different concentrations of HeLa cells that were unfixed or fixed with 1% formalin for 1 hour. The cells were processed using the methods of the invention.

GAPDH was detected in both the fixed and unfixed cells. A plot of the threshold cycle (Ct value) against cell concentration was linear up to 2,500 cells/µl for both the fixed and unfixed cells FIG. 2. The Ct values for both sets were nearly identical for both sets.

The cDNA synthesis reactions that did not include MMLV-RT (MMLV-RT minus control) did not generate any signal in the amplification reaction proving that the genomic DNA was degraded to undetectable levels and that signals produced by RT-PCR were attributable solely to the amplification of the cDNA.

The effect of fixing the cells up to 24 hours with a formalin concentration as high as 4% was tested. There was about a 1 Ct value shift between the fixed cells and the cells that were not fixed. This was most likely due to loss of cells from washing the cells twice more with 1×PBS to remove the formalin.

Those of skill would, based on this study, expect that this same procedure to function equally well with other types of common fixatives such as glutaraldehyde, acetic acid/ethanol (3:1), Carnoy's fixative, Bouin's fixative, and Osmium tetroxide fixative.

Example IV

Use of Methods on Fixed Cells Selected by Laser Capture Microdissection

To demonstrate the methods of the invention on fixed cells selected by laser capture microdis section, frozen sections of mouse kidney embedded with OCT media (Tissue-Tek), were fixed and stained with Hematoxylin-Eosin. Sections of 5 to 10 µm were produced with a cryostat. Areas of 0.04, 0.25, 0.6 and 1.0 mm² of tissue were captured by laser capture microdissection using an Arcturus PixCell II™ system, each on a different cap. The thin layer of plastic containing the tissue samples was removed and placed into an 0.5 ml centrifuge tube containing 100 µl Cell Lysis Buffer and 2 µl of the Armored RNA® control. The tubes were incubated at 75° C. for 10 minutes. The lysates were then subjected to DNase I treatment, reverse transcription, and PCR as described in EXAMPLE I. Primers and probes to detect a cyclophilin sequence as well as the Armored RNA® control were used in the PCR. Cyclophilin Primer and Probe sequences that may be employed were as follows: Forward: 5'-CCATCGTGTCATCAAGGACTTCAT-3' (SEQ ID NO. 10); Reverse: 5'-CTT GCC ATC CAG CCA GGA GGT CTT-3' (SEQ ID NO. 11); TaqMan Probe: 5'-(FAM)TG-GCACAGGAGGAAAGAGCATCTATG-(TAMRA)-3' (SEQ ID NO. 12). A Cyclophilin signal was detected in all samples. The Armored RNA® control ran alongside the cyclophilin reactions indicated that there was no inhibition from the tissue samples.

Example V

Multi-Well Format for Gene Expression Analysis

To demonstrate the methods of the invention in a multi-well format for gene expression analysis, cells were grown overnight in 0.2 ml DME media with 10% FBS with equal number of cells in each well in a 96 well culture plate (Falcon). The media was removed and the wells were washed with 0.2 ml 1×PBS, and the PBS was removed. One hundred µl of Cell Lysis Buffer was added to each well. The plate was then moved to a heating tile set to 75° C. and let stand for 10 minutes. To fully inactivate the proteinase K in the lysis, 2 µl of 0.1 M PMSF in DMSO was added to each sample and incubated at room temperature for two minutes. Two µl DNase I was added to each sample and the plate was incubated at 37° C. for 15 minutes while shaking. The plate was then moved again to the 75° C. heating tile for 5 minutes to inactivate the DNase I. One-step RT-PCR was performed on each lysate in a 96-well PCR plate as described in EXAMPLE IX.

In each sample GAPDH was detected by real-time PCR. An analysis of the Ct values for each sample gives a mean of 17.28 with a standard deviation of 0.524. This gives a CV of 3.03% with a high of 18.88 and a low of 15.90.

If one is using a heating tile that can be set to a higher temperature such, as 95° C., then it is possible to incubate the cells on these heating tiles to inactivate the proteinase K instead of adding PMSF. It is important that the samples themselves actually reach 75° C. when using proteinase K as the protease (other proteases may be inactivated at lower temperatures). If not, then some of the protease may remain active to digest the reverse transcriptase when the sample was incubated for cDNA synthesis. Such an event would lessen or completely diminish a signal from the sample.

Example VI

Use of Other Reverse Transcriptases in Context of Methods

MMLV-RT is one of the most commonly used reverse transcriptases by molecular biologists. However, there are other reverse transcriptases that function in the invention. For example, Avian Myelogenous Virus reverse transcriptase (AMV-RT; Retzel, 1980) and the Tth DNA polymerase, which also has reverse transcriptase activity, can each synthesize cDNA. Further, the DNA polymerase has reverse transcriptase activity if $Mn^{+2}$ is provided in the buffer (Myers, 1991) and can be used to generate cDNA from a cell lysate following the protocol of the invention. Those of skill in the art will understand that the above-described nucleic acid polymerases and any other nucleic acid polymerases having reverse transcriptase activity may be adaptable to the protocols of the invention.

Example VII

Different Concentrations of Proteinase K and Proteases Other than Proteinase K Function in Context of Methods of the Invention Using the procedure listed in EXAMPLE I, proteinase K has been used at concentrations of 25 and 500 µg/ml. The results have been essentially the same as using the 200 µg/ml concentration that was used in the standard protocol.

Proteases are classified into several groups based on the mechanism of catalysis. Serine proteases include but are not limited to Trypsin, Chymotrypsin, Elastase, Subtilisin, Streptogrisin, Thermitase, Aqualysin, and carboxypeptidase A, D, C, or Y. Cysteine proteases include but are not limited to Papain and Clostripain. Acid Proteases include but are not limited to Pepsin, Chymosin, and Cathepsin. Metalloproteases include but are not limited to Pronase, Thermolysin, Collagenase, Dispase, various aminopeptidases, and Carboxypeptidase A, B, E/H, M, T, or U. In some embodiments of the invention, these proteases or combination thereof could be used in place of or in addition to proteinase K. It is possible that a mixture of proteases could be used instead of a single protease to generate a cell lysate compatible with reverse transcription and PCR. In certain embodiments a protease or protease mixture may be used simultaneously with a nuclease, e.g., a DNase such as DNas I, or any other catabolic enzyme.

Example VIII

Tissue Samples

Another type of sample that may be used in regard to the invention is a piece of tissue consisting of cells ranging from hundreds to thousands. One such tissue or organ may be leech ganglia. Another sample type may be a patient needle biopsy that often consists of thousands of cells. A biopsy could be processed by the inventive methods and PCR amplified to make a diagnosis or prognosis by measuring the expression of certain genes. Another sample may be leukocytes or lymphocytes isolated from a blood sample. Plasma fractionated from a blood sample may be used in this invention to detect a virus such as HIV or HCV. Another sample may be whole blood itself.

Example IX

Coupling of Invention with One-Step RT-PCR

Methods of the invention can be used in a one-step RT-PCR reaction where the MMLV-RT and Taq polymerase were combined in a one tube, one buffer system. For example, HeLa S3 cells were grown, harvested, lysed, and DNase treated as in EXAMPLE I. Cell lysate concentrations of 1, 4, 20, 100, 500, 1,250, 2,500, 5,000, and 10,000 cells/µl were made and DNase treated as in EXAMPLE I. Five µl of each lysate was added to 2.5 µl 10×RT buffer (500 mM Tris pH 8.3, 750 mM KCl, 30 mM $MgCl_2$, 50 mM DTT), 1 µl (10 U/µl) of placental RNase Inhibitor (cat. #2687, Ambion, Inc.), 1 µl of MMLV-RT (25 U/µl), 4 µl dNTP mix (2.5 mM each), 0.5 µl 50×ROX standard (Ambion, Inc.), 1 µl PCR primer mix (10 µM mix of forward and reverse primers), 1 µl TaqMan probe (2 µM), 0.2 µl SuperTaq (Ambion, Inc.), and 8.8 µl RNase-free water (Ambion, Inc.). The reactions were placed in an ABI 7700 Prism thermocycler and the following profile was ran: 42° C., 15 minutes; 94° C., 2 minutes; [94° C., 20 seconds; 60° C., 20 seconds]×40 cycles.

GAPDH was detected in all samples that included HeLa cells. A plot of the threshold cycle (Ct value) against cell concentration was linear up to 2,500 cells/µl. GAPDH signal was detected at higher cell concentrations but inhibition of the reactions by higher cell concentrations was indicated by Ct values increasing at the higher cell concentrations compared to the lower concentrations.

The cDNA synthesis reactions that did not include MMLV-RT (MMLV-RT minus control) did not generate any signal in the amplification reaction proving that the genomic DNA was degraded to undetectable levels and that signals produced by RT-PCR are attributable solely to the amplification of the cDNA.

Example X

Use of Invention without the DNase Treatment

The DNase I step in some aspects of the invention is not necessary if the PCR primers used will not amplify genomic sequences. This can be done by designing primers that span an intron within the gene of interest. This greatly reduces the total time it takes to complete the procedure of the invention because the DNase I treatment can be eliminated.

For example, HeLa S3 cells were grown, harvested and lysed as described in EXAMPLE I. Reverse transcription followed by PCR was performed, again as in EXAMPLE I. A one-step RT-PCR procedure on the same lysates was performed as described in EXAMPLE IX using primers and probe for DDPK. DDPK Primer and Probe sequences, can be, for example: Forward: 5'-CTGGCCGGTCAT-CAACTGA-3' (SEQ ID NO. 13); Reverse: 5'-ACAAGCAAACCGAAATCTCTGG-3' (SEQ ID NO. 14); TaqMan Probe: 5'(FAM)-AATGCGT-(TAMRA)-CCT-GAGCAGCAGCCCp-3' (SEQ ID NO. 15). DDPK was detected by real time PCR, and the reverse transcriptase minus reactions were negative.

Example XI

RNA Amplification

There are many cases where researchers have a limited amount of sample and the RNA isolated from the sample is not enough to perform their desired assay. The technique that this applies to most often is producing a labeled nucleic acid from the isolated RNA and then hybridizing the labeled nucleic acid to a microarray. The signals produced at each of the addresses of the microarray indicate the level of expression for each of the genes on the array. Thus, a snapshot is taken of the abundance for each of the genes probed by the array.

Typically, the starting material for amplifying RNA is a minimum of ~10 ng of total RNA from the sample. Next, the RNA is reverse transcribed in the presence of an oligonucleotide primer that encodes an RNA polymerase promoter such as a T7 phage promoter. In the procedure by Kacian (U.S. Pat. No. 5,554,516), the material is now transcribed by T7 RNA polymerase to synthesize RNA. In the procedure by Phillips (1996), a second strand of cDNA is produced and then the double-stranded DNA is transcribed by a phage polymerase. Ambion, Inc. produces the MessageAmp kit (Cat. #1750) based on the procedure of Phillips (1996). Purified total RNA or poly(A)RNA is the recommended substrate for the MessageAmp kit.

Cell lysates generated by the Cells-to-cDNA II™ procedure were demonstrated to be suitable substrate for the MessageAmp kit. For example, K562 cells at concentrations of 200, 600 and 2,000 cells/µl were incubated at 75° C. for 10 minutes in a Cell Lysis Buffer comprised of 50 mM Tris pH 8.3, 75 mM KCl, 5 mM DTT, 1 mM EDTA, 1% TX-100, and 200 µg/ml proteinase K. No DNase I treatment was performed because it is not needed in this application. Five µl of each cell lysate concentration was used as the template in the MessageAmp procedure. RNA was amplified from 860 to 3,000 fold with this procedure (TABLE 1).

TABLE 1

Fold-Amplification of RNA from a Cell Lysate Generated by the Cells-to-cDNA II ™ method using the MessageAmp kit.

| Number of Cells Added to MessageAmp Reaction as Lysate | *Quantity of RNA in the Reaction (ng) | Quantity of RNA After MessageAmp Amplification (µg) | Fold-Amplification of Cellular RNA |
|---|---|---|---|
| 1,000 | 5 | 15 | 3,000 |
| 3,000 | 15 | 25 | 1,667 |
| 10,000 | 50 | 43 | 860 |

*Assume 5 pg of total RNA per cell

Example XII

Automation and Monitoring the Effects of Drug Treatment

Cells were grown overnight in 0.2 ml DME media with 10% FBS with equal number of cells in each well of a 96-well plate. After an overnight incubation, phorbol myristate acetate (PMA) is added to final concentrations of 100, 10, 1, 0.1, and 0 nM in the growth medium in replicates of eight. The cells were incubated at 37° C. for 24 hours. The 96-well plate and lid were placed on the Packard Multi-PROBE® II HT Liquid Handling System from PerkinElmer Life Sciences on the proper deck positions. All proceeding steps were entered into the WinPrep for automation. The growth medium was removed and the cells washed with 1×PBS. A volume of 0.1 ml Cell Lysis Buffer is added to each well. The plate was moved to a heating tile, for example, a tile at 75°, and incubated for 10 minutes. The plate was then moved to a shaker platform and 2 µl 100 mM PMSF in DMSO was added to each well to inactivate the proteinase K. PMSF is a serine protease inhibitor that does not inhibit reverse transcriptase or Taq polymerase. The plate was shaken for 2 minutes. PMSF can be used when the heating tile cannot heat the sample to 75° C. to inactivate the proteinase K. Two µl DNase I (2 U/µl) was added to each well and the plate was moved to a 37° C. heating tile. The plate was incubated for 15 minutes while shaking. The plate was then moved to a heating tile, for example, a tile at 75° C., and incubated for 5 minutes to inactivate the DNase I. The protocol for one step RT-PCR found in EXAMPLE IX was followed so that 20 µl aliquots of the master mix were added to a 96-well PCR plate. Five µl of lysate was added to each well. The plate was ready for one-step RT-PCR.

Figure 3:
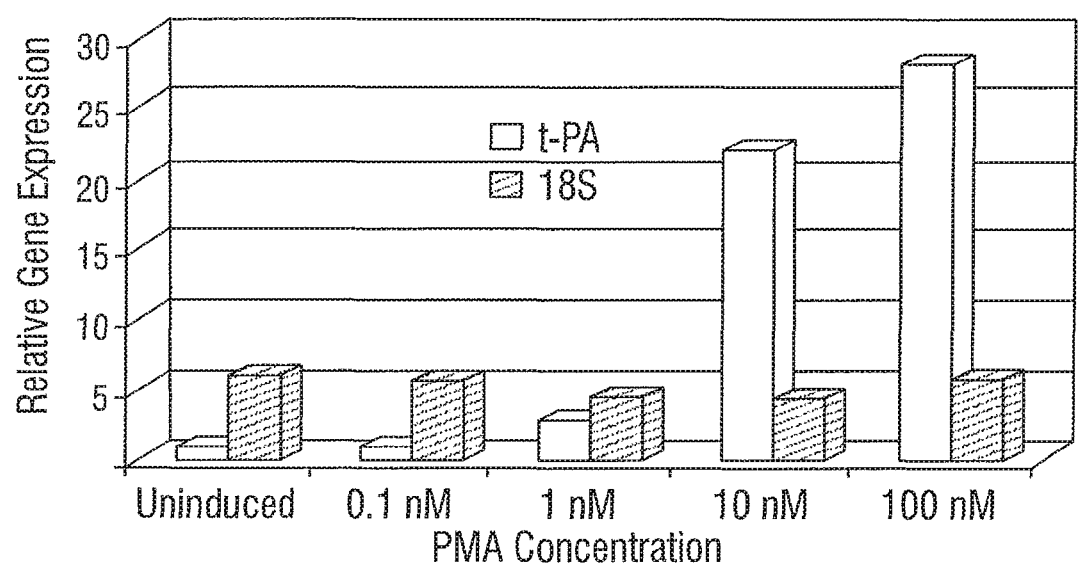
FIG. 3. Illustrates an example of measuring the levels of 18S rRNA and tPA mRNA in HeLa cells that were incubated with different concentrations of PMA by one-step, real-time RT-PCR in the ABI 7700. The cells were processed in 96-well plates using the methods of the invention.

The one-step RT-PCR was run with primers and TaqMan probes for both tissue plasminogen activator (t-PA) and 18S ribosomal RNA with a standard curve ran for each set. tPA Primer and Probe sequences were: Forward: 5'-GGCGCA-GTGCTTCTCTACAG-3' (SEQ ID NO. 16); Reverse: 5'-TAGGGTCTCGTCCCGCTTC-3' (SEQ ID NO. 17); TaqMan Probe: 5'-(FAM)-TTCTCCAGACCCACCACAC-CGC-(TAMRA)-3' (SEQ ID NO. 18); 18S Primer and Probe sequences: Forward: 5'TCAAGAACGAAAGTCGGAGG3' (SEQ ID NO. 19); Reverse: 5'GGACATCTAAGGGCAT-CACA3' (SEQ ID NO. 20); TaqMan Probe: 5'-(FAM)-TGGCTGAACGCCACTTGTCCCTCTAA-(TAMRA)-3' (SEQ ID NO. 21). The real-time PCR data shows there was about a 29-fold stimulation of t-PA with concentrations of 100 and 10 nM when the values were normalized to the levels of 18S rRNA which is assumed to be constant during different experimental conditions. FIG. 3.

Figure 4:
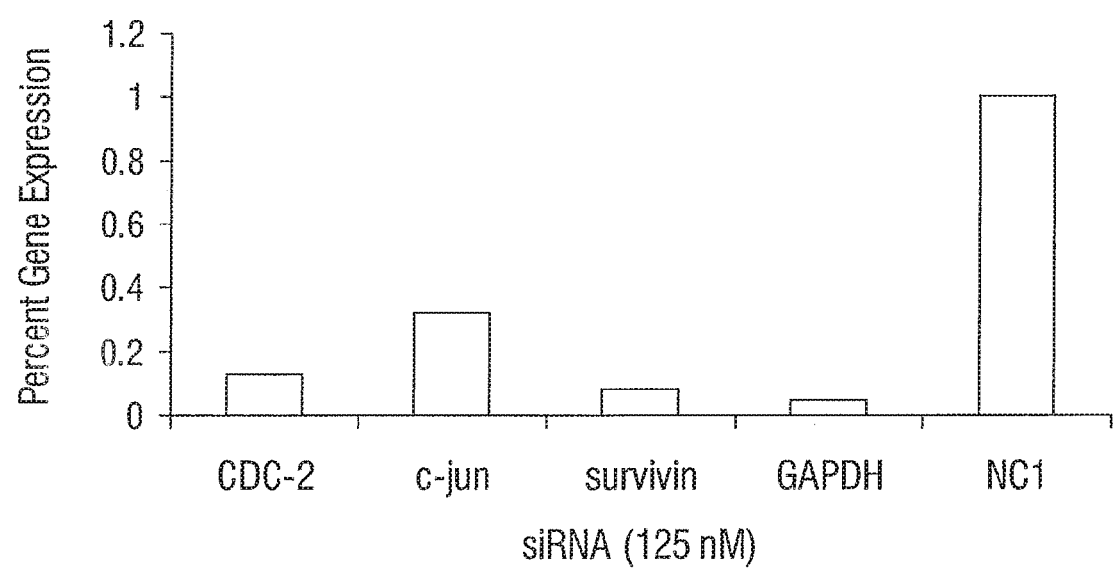
FIG. 4. Illustrates an example of analyzing Gene Silencing by siRNA using Cells-to-cDNA II™ Automated Protocol. HeLa cells were transfected with gene specific siRNAs against CDC-2, c-jun, survivin, and GAPDH or a negative control (NC1). After 48 hours, cells were processed according to the Cells-to-cDNA II™ automated protocol, and analyzed by real-time one-step RT-PCR for the indicated genes and normalized to 18S rRNA.

In a similar type of experiment, cells were treated with short interfering (si)RNA to down regulate specific genes (Elbashir, 2002). Three thousand cells grown in a 96-well dish were transfected with chemically synthesized, 125 nM gene-specific siRNAs against CDC-2, c-jun, survivin, and GAPDH or a negative control (NC1) 24 hours after plating using Oligofectamine transfection reagent (Invitrogen). After 48 hours, cells were processed according to the Cells-to-cDNA II™ automated protocol, and analyzed by real-time one-step RT-PCR on an ABI 7900 for the indicated genes and normalized to 18S rRNA. Gene expression was calculated as a percentage of gene expression compared with the negative control siRNA. Experiments were performed in replicates of eight. Using the cell lysate produced by the Cells-to-cDNA II™ procedure and one-tube RT-PCR, gene expression for each of the target genes was determined to be reduced by more than 70% (FIG. 4).

Example XIII

Multiple Enzymes Used to Produce the Cell Lysate

In addition to proteases, other types of enzymes may be included in the Cell Lysis Buffer, such as enzymes to digest nucleic acids, sugars, fats, connective tissue (collagen and elastin) and DNA. These enzymes may be more important with regard to EXAMPLE VIII where the system may be used for small quantities of tissue. A combination of enzymes may enhance the digestion process and also destroy the macromolecules that inhibit enzymatic reactions.

For example, the initial lysis step containing proteinase K was combined with the DNase treatment and the cellular DNA was digested to substantially reduce the signal generated in the reverse transcriptase minus reactions. This result was unexpected since it was thought that the proteinase K would digest the DNase I before the DNase could fully digest the cellular DNA. By combining these two enzymatic reactions, the Cells-to-cDNA II™ process is further streamlined and only a single incubation event is required to produce a cell lysate compatible with reverse transcription or one-step RT-PCR.

The Cell Lysis Buffer was made with proteinase K concentrations of 20 to 200 µg/ml and placed on ice. DNase I was added to the Cell Lysis Buffers at 0.1 U/µl and then the Cell Lysis Buffers were kept on ice while the cells were harvested. Cells were added to the different Cell Lysis Buffers at concentrations of 4 to 2,500 cells/µl. The samples were heated in a thermocycler at 60° C. for 10 minutes to give the DNase time to digest the cellular DNA before inactivating the proteinase K and DNase enzymes at 75° C. for 10 minutes. The same cells were also treated using the sequential method of EXAMPLE I. One-step real-time RT-PCR for GAPDH (as in EXAMPLE IX) was performed on these lysates. The difference between the RT minus and RT plus reactions were 18 Ct (~20,000×) indicating that the DNase I was active in the combined format and that the proteinase K did not digest the DNase until it had degraded nearly all of the cellular DNA (TABLE 2).

TABLE 2

Comparison of the signal obtained for GAPDH by real-time RT-PCR and PCR (RT−) using a combined or sequential proteinase K and DNase I treatments of HeLa S3 cells.

| Cell Concentration | Combined (Ct) | | Sequential (Ct) | |
|---|---|---|---|---|
| (cells/µl) | RT(+) | RT(−) | RT(+) | RT(−) |
| 4 | 21.3 | 40 | 21.4 | 40 |
| 20 | 17.6 | 40 | 18.1 | 40 |
| 100 | 16.9 | 31.9 | 15.7 | 33.5 |
| 500 | 14.6 | 33.3 | 14.1 | 36.7 |
| 2,500 | 12.9 | 31.5 | 12.7 | 31.7 |

Example XIV

Addition of Cell Lysis Buffer Directly to Tissue Culture Medium

Typically, the Cells-to-cDNA II™ procedure involves washing the cells grown in tissue culture with phosphate buffered saline (PBS), primarily to remove the serum from the sample that was in the growth medium. The serum can inhibit downstream enzymatic reactions like reverse transcription and PCR.

If the cells can be grown in serum-free medium, then the cell-washing step may be bypassed entirely. As such, the processing time will be decreased. Also, this procedure makes the handling of cells grown in suspension much easier because centrifugation is no longer required for washing. *Drosophila* cells are commonly grown in serum-free medium and therefore, the efficiency of the Cells-to-cDNA II™ procedure on these cells, if the cell washing step were omitted, was tested.

Schneider L2 *Drosophila* cells were grown to confluency in *Drosophila*-SFM (serum free medium). The cells were harvested in SFM and diluted to concentrations of 6,500; 1,300; 260; 52; and 10.4 cells/µl in SFM. Eighty µl of each cell concentration was added to a 0.5 ml tube to which two volumes (160 µl) of Cell Lysis Buffer was added. These samples were then taken through the Cells-to-cDNA II™ protocol including the DNase I digestion. The cell lysates were then used in one-step, real-time RT-PCR to detect Ubiquitin (accession #M22428) and analyzed using the ABI PRISM® 7900 HT Sequence Detection System Forward Primer: 5'-CACGCATCTTGTTTTCCCAAT-3' (SEQ ID NO:22); Reverse Primer: 5'-CTCGAGTGCGTTCGT-GATTTC-3' (SEQ ID NO:23); TaqMan Probe: 5'-AATTG-GCATCAAAACGCAAACAAATC-3' (SEQ ID NO:24). Lysate volumes of 5 µl were used in each of the 20 µl reactions.

It was found that all cell concentrations generated a PCR signal and that they were in the linear range. In addition, no signal was detected in the RT minus reactions indicating that the DNase treatment was effective in the presence of the SFM medium.

Example XV

Use of an Exemplary Kit for Producing cDNA from Mammalian Cells in Culture

Components of an exemplary kit for the preparation of cDNA from mammalian cells in culture may include one or more of the following reagents: 1×PBS (pH 7.4); Cell Lysis II Buffer (10 mM Tris pH 7.5, 3 mM MgCl$_2$, 1 mM CaCl$_2$, 1 mM EDTA pH 8.0, 1% Tx-100 and 200 ug/ml Proteinase K); DNase 1 (2 U/µl); 10×RT Buffer (500 mM Tris pH 8.3, 750 mM KCl, 30 mM MgCl2, 50 mM DTT); M-MLV Reverse Transcriptase; RNase Inhibitor (10 U/µl); dNTP Mix (2.5 mM each dNTP); Random Decamers (50 µM); Oligo(dT)$_{18}$ Primers (50 µM); Nuclease-free water; RNA control, e.g., Armored RNA control; control RNA primer pair, e.g., Armored RNA primer pair (10 µM each); and an endogenous Primer Pair (5 µM each). The kit components are supplied in suitable containers under suitable conditions for shipping or storage. The parameters for use of the kit components are described herein and may be used to produce cDNA from mammalian cells in culture without the isolation of mRNA. In certain embodiments, the cDNA produced may be used in a variety of assays or procedures including, but not limited to PCR amplification or automated PCR amplification and analysis in multiwell formats and RNA amplification.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Brady G, Iscove N N. Construction of cDNA libraries from single cells. Methods Enzymol. 225: 611-623, 1993.

Busche S, Gallinat S, Bohle R-M, Reinecke A, Seebeck J, Franke F, Fink L, Zhu M, Sumners C, Unger T. Expression of angiotensin AT1 and AT2 receptors in adult rat cardiomyocytes after myocardial infarction: a single-cell reverse transcriptase-polymerase chain reaction study. J. Am. Pathol. 157: 605-611, 2000.

Elbashir S M, Harborth J, Weber K, Tuschl T. Analysis of gene function in somatic mammalian cells using small interfering RNAs. Methods 26: 199-213, 2002.

Fink L, Kinfe T, Seeger W, Ermert L, Kummer W, Bohle R M. Immunostaining for cell picking and real-time mRNA quantitation. Am. J. Pathol. 157: 1459-1466, 2000a.

Fink L, Kinfe T, Stein M M, Ermet L, Hanze J, Kummer W, Seeger W, Bohle R M. Immunostaining and laser-assisted cell picking for mRNA analysis. Laboratory Invest. 80; 327-333, 2000b.

Klebe R J, Grant G M, Grant A M, Garcia M A, Giambernardi T A, Taylor G P. R T-PCR without RNA isolation. BioTechniques 21: 1094-1100, 1996.

Lockhart D J, Dong H, Byrne M C, et al. Expression monitoring by hybridization to high-density oligonucleotide arrays. Nat. Biotechnol. 14: 1675-1680, 1996.

Mesink E, van de Locht A, Schattenberg A, Linders E, Schaap N, Geurts van Kessel A, de Witte T. Quantitation of minimal residual disease in Philadelphia chromosome positive chronic myeloid leukemia patients using real-time quantitative R T-PCR. Br. J. Haematol. 102: 768-774, 1998.

Myers T W, Gelfand D H. Reverse transcription and DNA amplification by a Thermus thermophilus DNA polymerase. Biochemistry 30: 7661-7666, 1991.

O'Leary T J. Reducing the impact of endogenous ribonucleases on reverse transcription-PCR assay systems. Clin. Chem. 45: 449-450, 1999.

Pasloske B L, WalkerPeach C R, Obermoeller R D, Winkler M, DuBois D B. Armored RNA technology for the production of ribonuclease resistant viral RNA controls and standards. J. Clin. Microbiol. 36: 3590-3594, 1998.

Phillips J, Eberwine J H. Antisense RNA amplification: a linear amplification method for analyzing the mRNA population from single living cells. Methods 10: 283-288, 1996.

Retzel E F, Collett M S, Faras A J. Enzymatic synthesis of deoxyribonucleic acid by the avian retrovirus reverse transcriptase in vitro: optimum conditions required for transcription of large ribonucleic acid templates. Biochemistry 19: 513-518, 1980.

Sumida A, Yamamoto I, Zhou Q, Morisaki T, Azuma J. Evaluation of induction of CYP3A mRNA using the HepG2 cell line and reverse transcription-PCR. Biol. Pharm. Bull. 22: 61-65, 1999.

Su S, Vivier R G, Dickson M C, Thomas N, Kendrick M K, Williamson N M, Anson J G, Houston J G, Craig F F. High-throughput R T-PCT analysis of multiple transcripts using a microplate RNA isolation procedure. BioTechniques 22: 1107-1113, 1997.

Tang J, Hu M, Lee S, Roblin R. A polymerase chain reaction based method for detecting Mycoplasma/Acholeplasma contaminants in cell culture. J. Microbiol. Methods 39: 121-126, 2000.

Yan L, Kaczorowski G, Kohler M. One-tube protocol for single-cell reverse transcriptase-polymerase chain reaction. Anal. Biochem. 304: 267-270, 2002.

Roblin III R O, Hu M, Tang J S, Sunmin L. Mycoplasma polymerase chain reaction testing system using a set of mixed and single sequence primers. U.S. Pat. No. 5,693,467.

Van Gelder R N, von Zastrow M E, Barchas J D, Eberwine J H. Processes for genetic manipulations using promoters. U.S. Pat. No. 5,891,636.

Kacian D L, McAllister D L, McDonough S H, Dattagupta N. Nucleic acid sequence amplification method, composition and kit. U.S. Pat. No. 5,554,516.

Reynolds M A, Ruvolo M, Arnold Jr. L J. Combined polynucleotide sequence as discrete assay endpoints. U.S. Pat. No. 6,316,608.

What is claimed is:

1. A method for producing cDNA from at least one biological unit containing RNA, wherein the biological unit is a cell obtained from cell culture, from a tissue sample or from a body fluid, comprising:
    preparing an admixture comprising the biological unit, proteinase K and a deoxyribonuclease;
    incubating the admixture under conditions where the proteinase K and deoxyribonuclease are active;
    raising the temperature of the admixture containing the active proteinase K and deoxyribonuclease to 75 degrees C. to inactivate the proteinase K and the deoxyribonuclease;
    incubating the admixture with at least one reverse transcriptase under conditions to allow reverse transcription to produce cDNA;
    and
    further comprising amplifying the cDNA by real-time PCR.

2. The method of claim 1 wherein the deoxyribonuclease comprises DNase 1.

3. The method of claim 1, wherein the biological unit is a cell obtained from cell culture.

4. The method of claim 1, wherein the biological unit is a cell obtained from a tissue sample.

5. The method of claim 1, wherein the biological unit is a eukaryotic cell.

6. The method of claim 5, wherein the eukaryotic cell is a human cell.

7. The method of claim 1 wherein the biological unit is a prokaryotic cell.

8. The method of claim 1, wherein the biological unit is a fungal cell.

9. The method of claim 1, wherein the period for inactivation of the proteinase K and deoxyribonuclease at 75° C. is 10 minutes.

10. A method for producing cDNA for quantification of RNA from at least one biological unit containing RNA, wherein the biological unit is a cell obtained from cell culture, from a tissue sample or from a body fluid, comprising:
- preparing an admixture comprising the biological unit a deoxyribonuclease and at least one catabolic enzyme, wherein said enzyme is at least proteinase K;
- incubating the admixture under conditions where the proteinase K and the deoxyribonuclease are active;
- raising the temperature of the admixture to 75 degrees C. to inactivate the proteinase K and deoxyribonuclease;
- incubating the admixture with at least one reverse transcriptase under conditions to allow reverse transcription to produce cDNA.

11. The method of claim 10, wherein the biological unit is a cell obtained from cell culture.

12. The method of claim 11, further comprising amplifying the cDNA by real-time PCR.

13. The method of claim 10, wherein the biological unit is a cell obtained from a tissue sample.

14. The method of claim 10, wherein the biological unit is a eukaryotic cell.

15. The method of claim 14, wherein the eukaryotic cell is a human cell.

16. The method of claim 10, wherein the biological unit is a prokaryotic cell.

17. The method of claim 10, wherein the biological unit is a fungal cell.

18. The method of claim 10, wherein the period for inactivation of the proteinase K and deoxyribonuclease at 75 degrees C. is 10 minutes.

* * * * *